United States Patent [19]

Wandell

[11] Patent Number: Plant 7,655

[45] Date of Patent: Sep. 24, 1991

[54] ***ACER×FREEMANI* NAMED 'DTR 102'**

[76] Inventor: Willet N. Wandell, R.R. 1, Box 286, Oquawka, Ill. 61469

[21] Appl. No.: 487,882

[22] Filed: Mar. 5, 1990

[51] Int. Cl.[5] ..... A01H 5/00

[52] U.S. Cl. ..... Plt./51

[58] Field of Search ..... Plt. 51

*Primary Examiner*—James R. Feyrer

[57] ABSTRACT

This new variety of *Acer×freemani* was discovered in Urbana, Ill.; it shares some of the characteristics of both parent trees *Acer rubrum* and *Acer saccharinum* is a dense crown, heavy leaf population, substantial limb scaffold, rapid rate of growth, resistance to drought and winter crown damage, and a brilliant red fall color each October on all parts of the leaves on all ages of trees.

5 Drawing Sheets

BACKGROUND OF THE INVENTION

This variety of *Acer×freemani* was discovered by the applicant growing in a yard of a private residence in Urbana, Ill. The new variety exhibits a fast growth habit producing a broadly ovate crown with a heavy leaf population carried on a substantial limb scaffold. Further, this tree, through the years, has shown the ability to withstand drought and adverse environmental conditions, and exhibits no crown damage or breakage due to excessive snow loads normally periodically experienced in the central Midwest. Also, it has shown the ability to produce a bright crimson leaf color in October of each season, coloring simultaneously and producing this color on trees of all sizes. I have produced 200 trees in my nursery in Oquawka, Ill. by chip budding, obtaining buds from the parent tree; all progeny exhibited the characteristics of the parent tree.

SUMMARY OF THE INVENTION

This selection of *Acer×freemani* shares some of the characteristics of both parent trees (*Acer rubrum* and *Acer saccharinum*) responding with rapid growth, a broadly ovate crown, dense leaf population, intermediate terminal growth coloration, drought resistance and tolerance of adverse environmental conditions of its *Acer saccharinum* and simultaneous parentage.

Major scaffold branches are strongly ascending with crotch angles of approximately 20 degrees, compared with crotch angles of 45 to 60 degrees on silver maple and 45 to 55 degrees on red maple of same age and growing under similar culture; my new tree does not exhibit susceptibility to crown damage or any breakage due to excessive snow loads that are normally periodically experienced in central Illinois, reflecting a branch joint union of greater strength than the parent species, *Acer saccharinum.* Nursery liners produced by chip buds obtained from the parent tree maintain the approximately 20 degree crotch angle and the substantial limb scaffold more like the *Acer rubrum* parent species, but exhibit a hybrid vigor with five-years-old trees showing an average terminal growth of 45.6 inches, compared to an average of 24.3 inches of terminal growth on red maple of same age and growing with similar culture in my nursery in Oquawka, Ill. This vigor, coupled with the ascending branching and branch density, produces a distinctive tree with a controlled yet well-branched crown at an early age. Further, this terminal growth can be identified by an intermediate coloration that most closely corresponds to 176A of the *R.H.S. Colour*

*Chart,* The Royal Horticultural Society, London, England, as compared to the terminal growth color of the parent species, *Acer rubrum* (R.H.S. 183A), and to the terminal growth color of the parent species, *Acer saccharinum* (R.H.S. 172A). Also, branch collars on my new variety display a distinctive greyed-orange coloration (R.H.S. 165D), this coloration being absent on red maples and silver maples of same age growing with similar culture. October color on trees of all ages turns a persistant intense ruby red on trees of all sizes.

DESCRIPTION OF THE NEW PLANT

Figure 1:
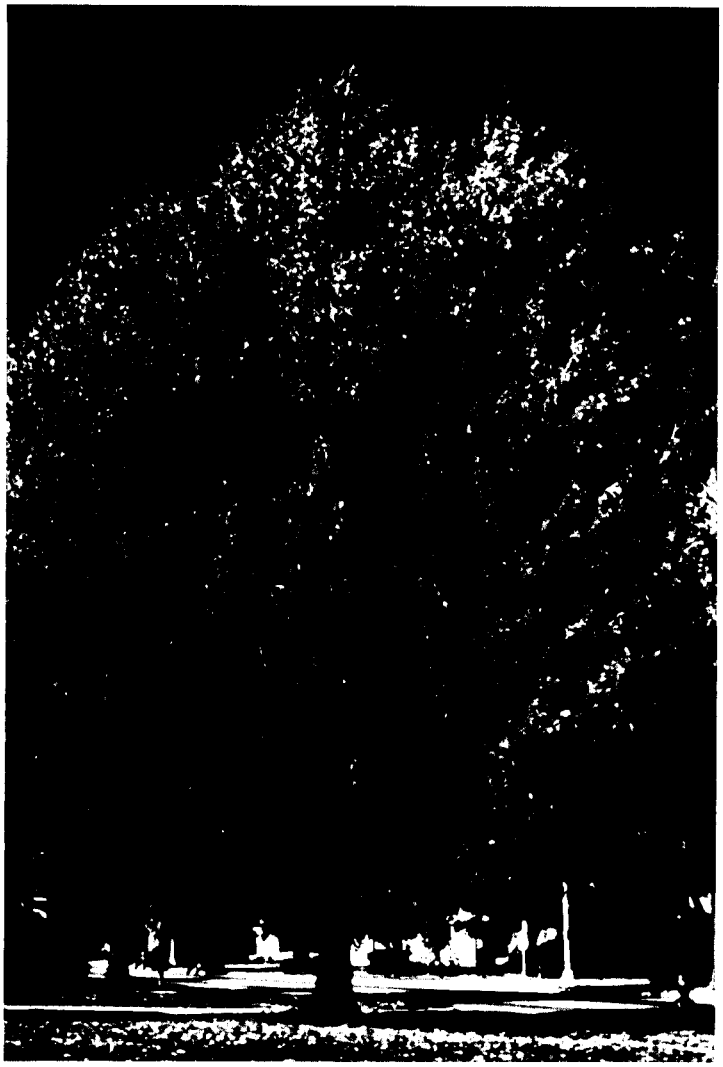
FIG. 1: Is a photographic view of my new variety as it appears in October showing overall bright crimson leaf color.
Figure 2:
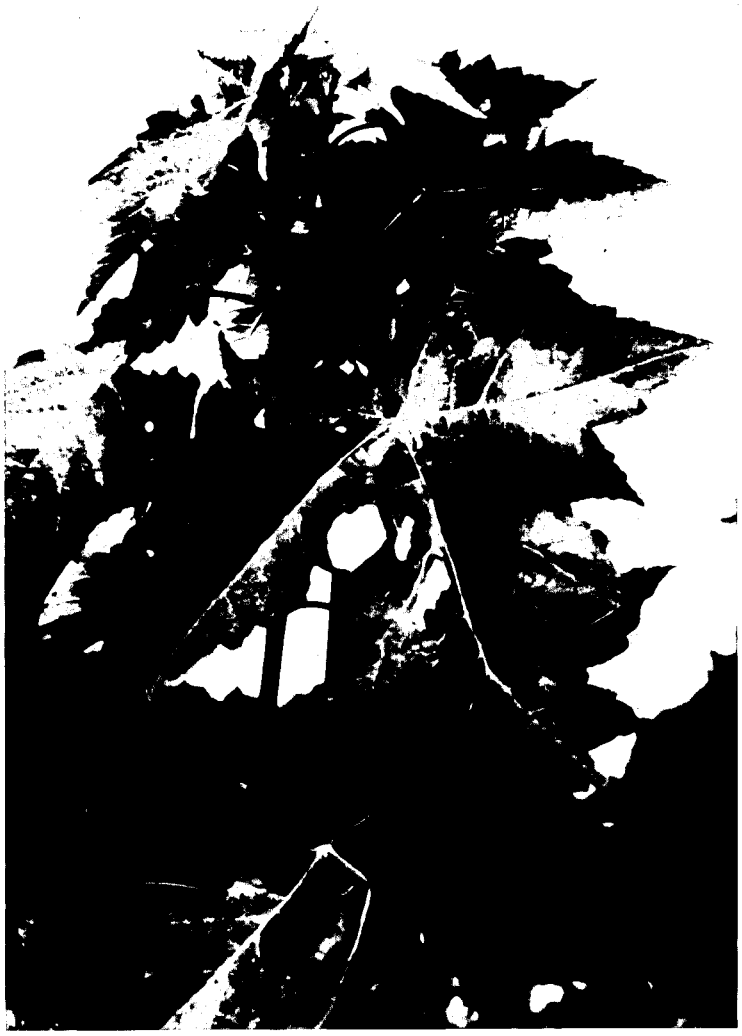
FIG. 2: Is a photographic view of my new variety as it appears in mid-summer.
Figure 3:
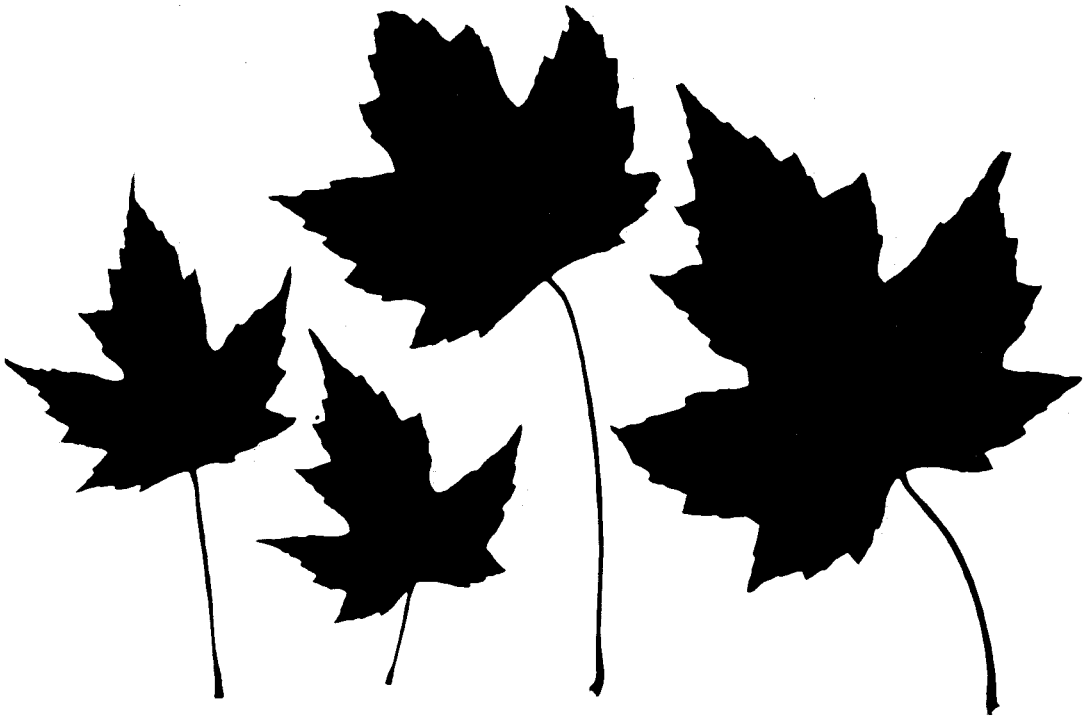
FIG. 3: Is a photographic view of some individual leaves as they fall from the tree in early November, 1988.
Figure 4:
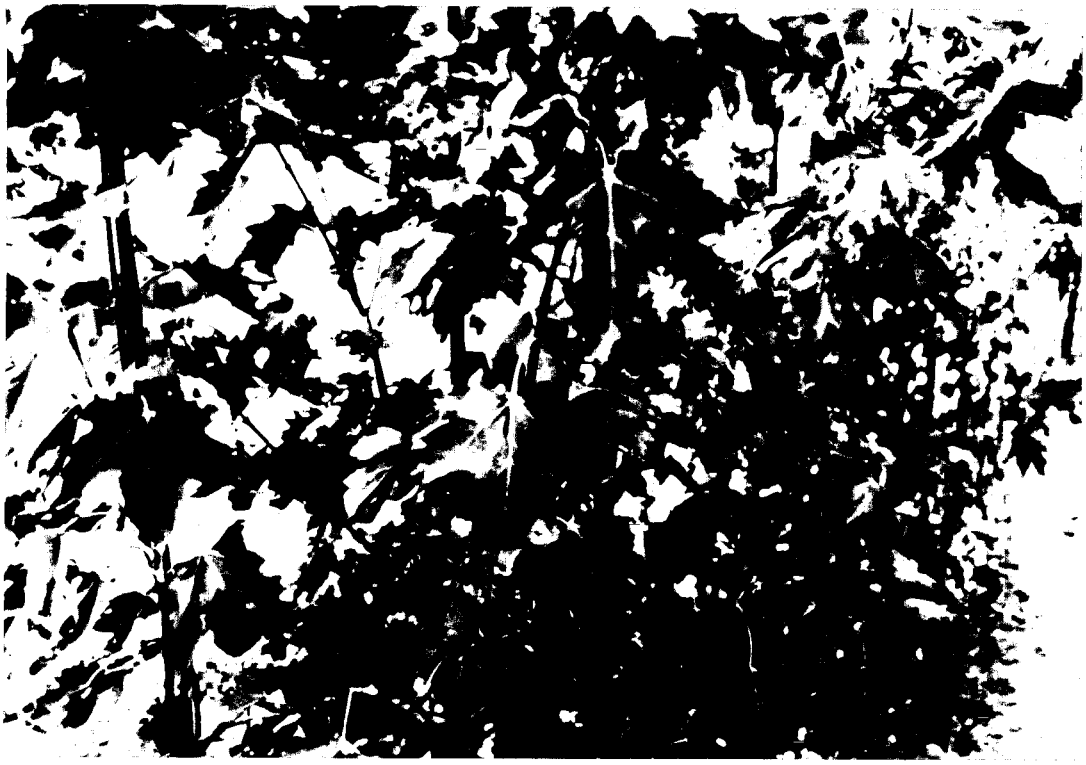
FIG. 4: Is a photographic view showing the heavy leaf population and substantial limb scaffold and vigorous growth of two-years-old trees in the nursery.
Figure 5:
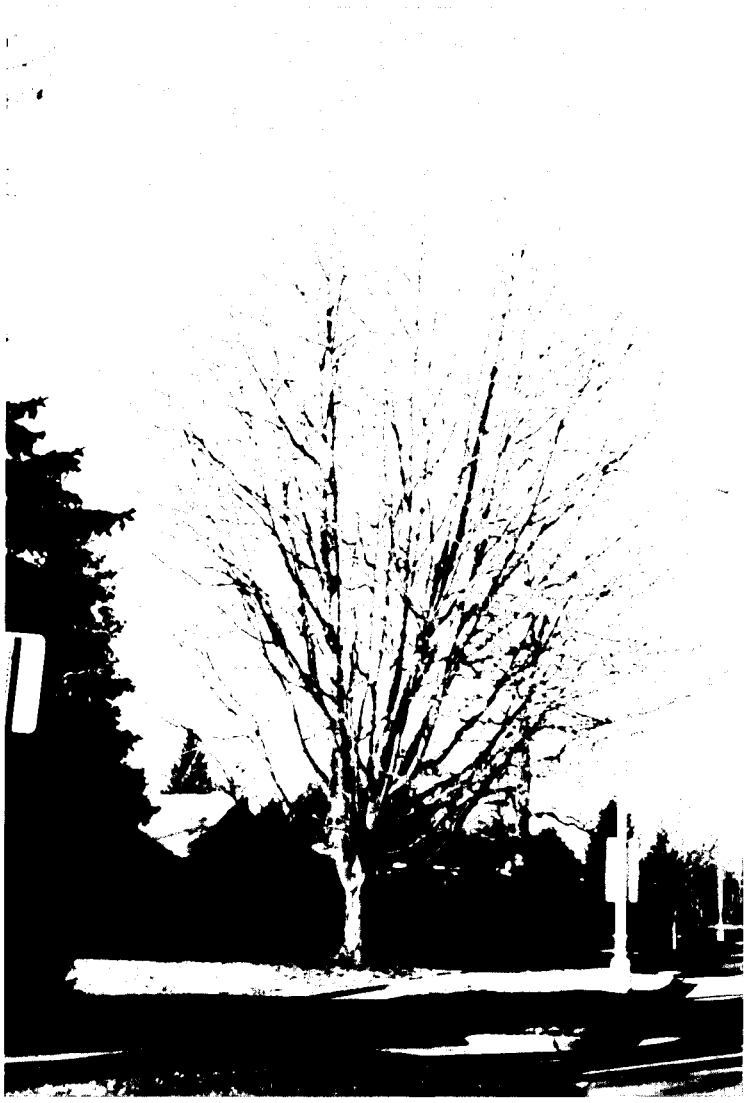
FIG. 5: Is a photographic view showing the tree in dormant condition.

The following is a detailed description of my new variety of *Acer×freemani,* the stated observations having been made on trees in Urbana, Ill. and Oquawka, Ill. by the applicant and found to distinguish from the species.

Origin: A tree of unknown origin, a hybrid between red maple (*Acer rubrum*) and silver maple (*Acer saccharinum*) found in a yard of a private residence in Urbana, Ill.

Classification: *Acer×freemani.*

Parentage: A sport of red maple (*Acer rubrum*) and silver maple (*Acer saccharinum*).

Form: Broadly ovate.

Habit: A deciduous tree with a short single trunk, a central but not dominant leader and numerous, strongly ascending main and secondary branches, with none descending, and the branching habit appearing intermediate of the two parent species, but with a higher density of branching than normally seen in either parent species; crown broadly ovate in shape, symmetrical and dense; major scaffold branches are strongly ascending with crotch angles of approximately 20 degrees; rapid growth and drought tolerance of silver maple but not exhibiting crown breakage or damage due to excessive snow loads. Mature tree height of 74 feet and a crown spread of 54 feet, most closely resembling the parent *Acer saccharinum* in ultimate size. Juvenile trees produced from chip buds obtained from the parent tree maintain the higher density of branches and the approximate 20 degree crotch angle, growing vigorously as expressed in inches of terminal growth, the average being 45.6 inches per year.

Twigs: Moderately stout, 2.5–4 mm in diameter, glabrous, orange-reddish-brown (R.H.S. 176A), lustrous, marked with tan, hyaline-margined, elliptic lenticels, with a slight disagreeable odor when crushed; outermost twigs curved upwards. Leaf scars opposite, C-shaped, connected by a fine line, with 3 bundle traces, stipule scars lacking.

Winter buds: Two types are present. Vegetative buds 3.5–5 mm long, rounded at tips, laterally flattened, sessile, bright purple-red (R.H.S. 183B), glabrous, with 2 pairs of exposed, blunt, ciliate scales. Flower buds 3–4 mm in diameter, globose, very shortly stalked, bright to dark red-purple (R.H.S. 182A), some with adpressed orange hairs, with 2–4 pairs of exposed bud scales, forming whorled clusters around the twigs.

Bark: Smooth, thin and medium grey on branches and juvenile trees, like a red maple but differing in color in that the selection corresponds to R.H.S. 201C with brown-grey undertones most nearly resembling R.H.S. 199A. Branch scars on juvenile trees a greyed-orange color (R.H.S. 165D). Bark on the trunk of the mature tree is darker than its branches (R.H.S. 198A), with large, flat, thin scales that peel away at the bottom, like a silver maple.

Leaves: Oppositely arranged, deciduous, simple, resembling those of a silver maple; blades palmately and deeply 3–5 lobed, 7–10 cm long and 7–12 cm wide, the tips long acuminate, the margins coarsely double-serrate, the bases rounded-truncate to shallowly cordate; leaf surface lustrous green above like a red maple (R.H.S. 137A), silvery below like a silver maple (R.H.S. 147B); petioles slender, flattened, 2.5–9 cm long, most nearly resembling the silver maple parentage.

Flowers: Nearly sessile, the pedicels 1–2 mm long; calyx cup 1.5 mm long; petals absent; ovary pubescent with long trichomes, the stypes 5 mm long. The dates of flowering not noted, flowering observed at the usual time of early April in central Illinois.

Fruit: Schizocarps splitting apart into two samaras, the sinus between the samaras V-shaped; each mericarp 4–5 cm long. Date of seed fail has not been recorded. The fertility of the seed is not known.

Fall color: Has the red color of a red maple with all parts of all leaves on all aged trees turning a uniform red color most closely resembling R.H.S. 60B. The young trees also have a similar red fall color.

I claim:

1. A new and distinctive variety of *Acer×freemani* named 'DTR 102', as described and illustrated herein, that differs from all other varieties by the unique combination of characteristics intermediate between red and silver maples with (1) simultaneous red fall color on all leaves of all ages of trees; (2) broadly ovate crown, short trunk, central but not dominant leader, and numerous ascending main branches; and (3) drought resistance and rapid growth of silver maple without the susceptibility to crown damage or breakage due to excessive snow loads.

* * * * *